(12) United States Patent
Hansen et al.

(10) Patent No.: US 8,927,265 B2
(45) Date of Patent: Jan. 6, 2015

(54) HUMAN WASTE TREATMENT SYSTEM AND METHOD

(75) Inventors: Jaron C. Hansen, Springville, UT (US); Lee D. Hansen, Saratoga Springs, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 13/444,904

(22) Filed: Apr. 12, 2012

(65) Prior Publication Data

US 2013/0130346 A1 May 23, 2013

Related U.S. Application Data

(60) Provisional application No. 61/517,085, filed on Apr. 13, 2011.

(51) Int. Cl.
| | |
|---|---|
| *C12M 1/02* | (2006.01) |
| *C12M 1/10* | (2006.01) |
| *B09B 3/00* | (2006.01) |
| *C12M 1/107* | (2006.01) |
| *C02F 3/28* | (2006.01) |
| *B60R 15/04* | (2006.01) |
| *C02F 3/00* | (2006.01) |
| *C02F 1/04* | (2006.01) |
| *C02F 103/00* | (2006.01) |

(52) U.S. Cl.
CPC .................. *B09B 3/00* (2013.01); *C12M 21/04* (2013.01); *C02F 3/28* (2013.01); *B60R 15/04* (2013.01); *C02F 3/00* (2013.01); *C02F 1/048* (2013.01); *C02F 2103/005* (2013.01); *C02F 2203/008* (2013.01)
USPC ........................................ 435/290.2; 435/167

(58) Field of Classification Search
CPC .......... C12M 21/04; C02F 3/34; C12P 5/023; Y02E 50/343
USPC ................................................ 435/167, 290.2
See application file for complete search history.

(56) References Cited

U.S. PATENT DOCUMENTS

| | | | |
|---|---|---|---|
| 3,950,249 A * | 4/1976 | Eger et al. ..................... 210/104 |
| 4,210,528 A | 7/1980 | Coviello | |
| 4,491,522 A | 1/1985 | Ishida | |
| 4,904,387 A | 2/1990 | Jordan | |
| 7,452,467 B2 | 11/2008 | Hansen | |
| 2003/0070986 A1* | 4/2003 | Braun ........................... 210/620 |
| 2007/0214565 A1* | 9/2007 | Matejka ........................... 4/661 |
| 2008/0289497 A1* | 11/2008 | Barclay et al. .................. 95/114 |
| 2011/0041689 A1 | 2/2011 | Hansen | |

OTHER PUBLICATIONS

Melvin S. Finstein. "Anaerobic Digestion Variants in the Treatment of Solid Wastes." Microbe. vol. 5, No. 4, Apr. 2010. American Society for Microbiology.*
Loowatt, "How it Works," downloaded from Internet Oct. 11, 2012, http://www.loowatt.com/toilets/.
Go Green Solutions Pvt. Ltd., "Deluxe Type Mobile Toilet Trailer," downloaded from Internet Oct. 11, 2012, http://www.gogreensol.com/images/Mobile%20Toilet%20Trailer%20Brochure.pdf. 2 pages. Published in Nagpur.

* cited by examiner

*Primary Examiner* — Michael Hobbs
(74) *Attorney, Agent, or Firm* — Jacob C. Ong (57) ABSTRACT

A human waste treatment system is disclosed that includes at least one waste receptacle such as an airline-style toilet, an anaerobic digester such as an induced bed reactor, and a gas conditioner. Human waste may be moved by a macerator pump. Inside the digester, bacteria digests organic solids to form biogas. The anaerobic digester may be operated at thermophilic temperatures to kill pathogenic bacteria in the waste and produce treated water. The gas conditioner purifies the biogas which may be used to power an electric generator. Treated water may be used to flush the system. The system may be mounted on a semi-truck trailer and transported. The system may be self-contained.

6 Claims, 3 Drawing Sheets

HUMAN WASTE TREATMENT SYSTEM AND METHOD

CROSS REFERENCE TO RELATED APPLICATION

This application claims the benefit of the provisional patent application with Ser. No. 61/517,085 which was filed on Apr. 13, 2011.

STATEMENT REGARDING FEDERALLY SPONSORED RESEARCH OR DEVELOPMENT

This invention was not made with federal government support.

TECHNICAL FIELD

Methods and apparatus are disclosed for the treatment of wastewater. Portable processes, devices, and systems for anaerobic digestion of human waste and using biogas formed from the digestion as an energy source are disclosed.

BACKGROUND OF THE INVENTION

Wastewater treatment has always been important, particularly for water containing human waste, which can spread dangerous diseases. Traditional methods of dealing with human waste include indoor toilets, municipal sewage systems, septic tanks, and other such systems and infrastructure. These systems serve the important functions of removing human waste from living areas and transporting it to facilities where it can be disposed of or treated.

Human waste can become problematic when the normal facilities for waste removal and treatment are unavailable. This might occur after a natural disaster or political upheaval. In these situations, the normal waste removal systems such as sewers may be disrupted, leaving the population to find other ways to dispose of waste. Disposing of human waste directly into the environment without any treatment can lead to the spread of disease. In disaster situations, problems with the spread of disease can be compounded by scarcity of resources such as water, electricity, and fuel.

More sanitary methods of disposing of waste include digging latrines and using portable toilets with waste storage tanks. However, these solutions have the disadvantages of unpleasant odors and a limited capacity. Portable toilets with storage tanks can only hold a finite amount of waste before they must be transported to a location where the waste can be disposed of safely.

An anaerobic digestion process is a fermentation process which has been used to treat organic waste such as human waste, livestock waste, and sewer sludge. See U.S. Pat. No. 4,491,522. Through anaerobic digestion, organic matter is partially removed from wastewater by converting at least some of the organic matter into biogas. Anaerobic digestion has been accomplished through the use of bioreactors into which wastewater is fed. One particular type of bioreactor, called an induced sludge blanket reactor, induced bed reactor, or IBR, is disclosed in U.S. Pat. No. 7,452,467, which is incorporated in its entirety into this application. IBRs are often installed near farms or other facilities that produce large amounts of organic waste. They are installed as permanent fixtures, often with a small building enclosing them. As used herein, the term "anaerobic digester" refers to a reactor in which a pretreated substance can be placed and anaerobic organisms are allowed to convert the pretreated substance into bioenergy. As used herein, the term anaerobic digester encompasses "partially-anaerobic digesters" which are similar to an anaerobic digester; however, the reactor may be specifically designed to accommodate mixed cultures of aerobic and anaerobic organisms. The anaerobic and aerobic organisms can include, but are not limited to archaea, bacteria, yeast, fungi, plant cells, animal cells and genetically-engineered organisms which are selected for their ability to bioconvert the substrate and produce a selected product. Non-limiting examples of anaerobic and partially-anaerobic digesters include: anaerobic activated sludge process, anaerobic clarigester, anaerobic contact process, anaerobic expanded-bed reactor, anaerobic filter, anaerobic fluidized bed, anaerobic lagoon, anaerobic migrating blanket reactor, batch system anaerobic digester, continuous stirred-tank reactor (CSTR), expanded granular sludge bed digester, hybrid reactor, Imhoff tank, induced blanket reactor, internal circulation reactor (IC), one-stage anaerobic digester, partial mixing anaerobic digester, submerged media anaerobic reactor, two-stage anaerobic digester, upflow anaerobic sludge blanket, upflow and down-flow anaerobic attached growth digester, etc.

One useful aspect of anaerobic digestion is its ability to produce biogas. Biogas is a methane-rich product of anaerobic digestion, produced by bacteria as they break down the organic matter in a bioreactor. Biogas can be used as a fuel, to provide on-site heating or electricity generation. As a consequence of the digestion process, biogas can contain high concentrations of hydrogen sulfide, carbon dioxide, and water. Downstream utilization of the methane produced from the digestion process has been hindered by the high concentrations of these impurities. For example, use of unpurified biogas to drive engine turbines can quickly lead to corrosion (e.g., pitting) of the turbine or other engine components. Biogas has been purified through a method disclosed in the U.S. patent application entitled "Off Gas Purification," (Pub. No. US 2011/0041689 A1) which is incorporated in its entirety into this application. After being purified, the biogas is much more useful for applications such as heating and electricity generation.

SUMMARY OF THE INVENTION

Methods and apparatus relating to portable processes, devices, and systems for anaerobic digestion of human waste, purification of biogas from the digestion process, provision of sanitary, treated water, and provision of power for services outside the system such as electrical, heating and lighting are disclosed. The methods and apparatus disclosed herein are related to providing a reliable, sanitary, and economical way to handle human toilet waste and to provide an auxiliary power source in situations when other services are unavailable, such as after a disaster. This might be the case after a hurricane or due to political upheaval in a remote part of the world. The disclosed methods and apparatus could also be used by a military unit that desired to provide convenient modern odor free toilets with a power source in a bivouac situation. The invention might also be useful at large public gatherings, such as sporting events, conventions or locations where a high concentration of people are found. The invention renders human waste safe for final disposal and it is beneficial to cropland and gardens.

If there is a conflict between the definitions found within this paragraph and the definitions used in other paragraphs, the definitions that are used in this paragraph shall govern. Another purpose of the present invention is to provide biogas as an energy source. A waste treatment system may utilize biogas from the digestion process to generate sufficient power to operate the system, allowing the system to be self-contained with respect to energy (referred to as a "biogas energy self-contained apparatus"). A waste treatment system may utilize biogas from the digestion process and other sources of renewal energy, such as solar power, to allow the system to be self-contained with respect to energy (referred to as an "energy self-contained apparatus"). An energy self-contained waste treatment system or biogas energy self-contained waste treatment system may produce sufficient energy so that the waste treatment system can treat the human waste to produce sufficient water to flush the system without additional water (referred to as a "self-contained water-from-human-waste apparatus") or with only the addition of rainwater which may or may not be treated with a filter (referred to as a "self-contained water apparatus"). For example, biogas may power an electric generator that supplies electricity to various pumps, equipment, and lighting within the system. Biogas may also be used as a power source for other systems, external to the waste treatment system. For example, a biogas powered electric generator may provide electricity to nearby buildings. Such a generator might provide power to a field hospital or machine shop. Biogas may also be burned to provide heat or lighting, or stored and transported to other locations to be used as fuel. In some embodiments, biogas that has been purified may then be used as fuel for a methane fuel cell, and the methane fuel cell can then be used to produce electricity.

Another purpose of the present invention is to provide a self-contained waste treatment system. The system may treat wastewater from flushing toilets and recycle the water back to the toilets for further flushing. Thus the system may operate without any external water supply. Likewise, the system may generate electricity from biogas to power the various pumps, equipment, and lighting within the system. Thus the system may operate without any external power supply. Because the system is self-contained, it may be used in remote locations where water and power are not available.

One embodiment of the present invention involves a portable waste treatment system mounted on a semi-truck trailer. In one embodiment the system includes 22 toilet stalls on the lower deck of a drop-deck trailer; other embodiments of the system may include less or more toilets. When a user flushes a toilet, the wastewater is carried into a gravity flow pipe. The gravity flow pipe leads to a pump box, where the wastewater is collected in a holding tank. Wastewater is removed from the holding tank by a pump, such as a macerator pump, which breaks up solids in the wastewater and pumps it into the bottom of an IBR situated on the upper deck of the trailer. Bacteria inside the IBR break down organic solids in the wastewater, producing biogas and treated water. Biogas from the IBR is purified by a gas conditioner, and may then be fed to a system for heating the IBR when necessary to keep the bacteria at their optimal growth temperature. Treated water leaves the IBR through the IBR's effluent stream, and is collected in a water collection tank. A pump draws water from the water collection tank and pumps it into a central flush water pipe, which supplies water for flushing the 22 toilets on the lower deck of the trailer.

The methods and apparatus as disclosed herein may also be used to construct a non-portable waste treatment system such as an outhouse with only 1 toilet, an outhouse with 10 toilets, an outhouse with 50 toilets; the methods and apparatus as disclosed herein may also be used to construct a portable waste treatment system that uses a platform on wheels, a platform on sled runners, or an individual portable toilet system.

DETAILED DESCRIPTION OF THE INVENTION

1. Overview

Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. Unless otherwise specified, the steps of a method may be conducted in any order.

References throughout this specification to "one embodiment," "an embodiment," "at least one embodiment," and the like mean that the disclosed features may be contained in a particular embodiment of the present invention. All such references may refer to separate, specific embodiments, and these references do not necessarily all refer to the same embodiment. Any disclosed steps, features, structures, characteristics, and details may be combined in any suitable way, and the present invention includes all such combinations that are covered by the claims.

Some of the processes and devices incorporated in the present invention have already been proven useful in treating wastewater. These processes and devices include the following: collection of human waste using standard aircraft style toilets; transporting waste via standard sanitary pipe; and treating waste in an anaerobic digester subsystem. The present invention also involves the collection of some of the pathogen free and low odor effluent water from the anaerobic digester for recycle in flush style toilets. Additionally, the anaerobic digester will produce methane-containing "biogas" as a byproduct of waste treatment. Methane is the primary component of natural gas and thus biogas can be used in place of natural gas or as a renewable energy resource. Biogas contains trace amounts of smelly and toxic gases that will be removed in a gas conditioner, which may contain a regenerable zeolite bed. Purified biogas may be used to power an electric generator, which in turn may provide electricity to pumps, the anaerobic digester, and the gas conditioner. Biogas may also be used to power external systems, such as providing electricity, heat, or lighting to nearby buildings. Otherwise, excess unused cleaned biogas can be flared. Excess unrecycled water may serve as fertilizer or soil conditioner on gardens or other crops or land applied, be used to water crops or gardens, placed in an evaporation pond, or be added to an existing wastewater treatment system.

In some embodiments, a waste treatment system may be mounted on a trailer which can be towed behind a truck or other vehicle. For example, in at least one embodiment of the present invention, a waste treatment system is mounted on a standard, 48' drop-deck semi-truck trailer. The trailer may be 102" wide. The lower deck of the trailer may be 38' long, and the upper deck may be 10' long. In addition to various sizes of drop-deck trailers, in various embodiments waste treatment systems may be mounted on other bases. For example, a system might be mounted on a different type of semi-truck trailer, or a shipping container. A system might be mounted on any type of large shipping container, for example, a standard 20° shipping container or a standard 40' shipping container. Using different bases for mounting a system would allow for different means of transportation for delivering the system to a location where waste treatment is needed. An advantage of the present invention is that waste treatment systems may be transported by truck, train, ship, plane, or other modes of transportation that can carry a trailer or shipping container, allowing the waste treatment to be delivered to a location where it is needed.

A waste treatment system in accordance with the present invention includes at least one waste receptacle, configured to receive human waste. For example, the system may include one or more toilets. In some embodiments, toilets may be arranged in one or more rows and enclosed in stalls to provide privacy. For example, in one particular embodiment, two rows of 11 toilet stalls are disposed on the lower deck of the trailer. Each stall comprises a toilet disposed on the bed of the trailer, a left wall, a right wall, a rear wall, a door, and a ceiling. The ceiling and rear wall for an entire row of stalls may comprise single pieces, with the left and right walls of each stall being formed from dividers disposed between the toilets. The doors may have a smaller dimension of height than the stalls, and be attached to the stalls by hinges that allow the doors to swing open, the hinges being disposed such that there is an under-door space beneath the doors and an above-door space above the doors. The under-door and above-door spaces may allow for more air circulation inside the stalls and also provide a way to enter if a stall is accidentally locked closed with no one inside.

Toilets of various types may be included in various embodiments. For example, the toilets may airliner-style toilets, which use pressurized water to flush and close while flushing so the user does not see the water used to flush. In other embodiments, other types of toilets may be used, such as toilets with gravity-powered flushing and water reservoirs. Toilets may be syphoning, non-syphoning, or vacuum toilets. Toilets may be various sizes, for example, between 13" and 17" wide, between 14" and 16" wide, or 15" wide.

In some embodiments, other types of human waste receptacles, such as urinals, may be substituted for some of the toilets. Some of the toilets in a waste treatment system might be replaced by one or two urinals. If two urinals are used in one stall in place of one toilet, a privacy divider may be added between them.

Stalls may be various sizes, depending on the number of waste receptacles in the system and the size of the system. For example, in one particular embodiment each stall is about 41" wide, allowing for a row of 11 stalls placed side by side on the 38' lower deck of the trailer. However, the size of the stalls may be varied and the size of the trailer may be varied. One will appreciate that this would allow for other numbers of stalls. For example, on a 38' lower deck there might be a row of 10 stalls that are 44" each, or 12 stalls that are 36" wide each. Stalls may be any suitable width, for example, between 36" and 48" wide, or between 40" and 44" wide, or between 40" and 42" wide. Any suitable length of lower deck could be used as well, for example, between 30' and 50', or between 35' and 40', or between 36' and 38'.

The depth of stalls may also vary depending on the size of the system, the size of waste receptacles used, and number of rows of stalls. For example, in one particular embodiment, the stalls are 45" deep from front to back. On a 102"-wide trailer this allows for two rows of stalls with a 12" space between the rows. In at least one embodiment, the rows of stalls both face outward, with their rear walls forming a 12" space between the rows at the center of the trailer. In other embodiments, the number and orientation of rows could be different. For example, if the trailer were wider, the rows might face toward the middle of the trailer, where there would be room for a walkway between the rows. Or on a narrower trailer, there may only be a single row of stalls. Also, the front-to-back depth of the stalls may vary, for example, depth may be between 40" and 50", or between 43" and 47", or between 44" and 46".

Water may be required to flush waste receptacles in waste treatment systems in accordance with the present invention. Water for flushing is recycled from the anaerobic digester, and may be delivered to the waste receptacles in various ways. In some embodiments, one or more pumps may supply water to the waste receptacles. For example, in one particular embodiment water for airliner-style toilets is supplied by a 500 W flush water pump, which pressurizes the water to above 35 psi (242 kPa). Water is pumped from the flush water pump to the toilets through one or more central flush water lines. All toilets in the system are connected, in parallel, to the central flush water lines by upper connecting pipes which run from the central flush water lines to the toilets. Each toilet has a flush valve which remains closed until a user flushes the toilet. The closed flush valves allow the system to retain the pressure in the central flush water line above 35 psi. In other embodiments, water pressure may be provided by gravity instead of a pump. However, in gravity-powered embodiments the water pressure would likely be much lower (80 feet of drop would be required to achieve 35 psi pressure). Therefore, flush toilets with flush water reservoirs would need to be used instead of toilets that flush using pressurized water. Embodiments with airliner-style toilets that flush with pressurized water provide the advantages that the amount of water used per flush may be less than for toilets with water reservoirs (pressurized water toilets may use 0.5 to 1 gal of water per flush, whereas toilets with water reservoirs may require 3 to 5 gal per flush) and the user will not see the recycled flush water, which may have a brown or black appearance even though it is treated and pathogen-free. As used herein, "treated" material means a state in which most or all of the pathogens present in the material have been inactivated or destroyed. Thus, "treated" water refers to water in which most or all of the pathogens in the water have been either destroyed or inactivated. "Treated" waste refers to waste, such as human waste, in which most or all of the pathogens in the waste have either been destroyed or inactivated.

Waste treatment systems in accordance with the present invention include a means for transporting wastewater from waste receptacles to an anaerobic digester. In some embodiments, wastewater may be pumped from the outlet of one or more toilets to the anaerobic digester. The wastewater pump may include a device for breaking up solids in the wastewater stream, such as a macerator. Piping may connect the one or more toilets to the pump so that wastewater can flow from the toilets to the pump. For example, in one particular embodiment, toilets mounted on a trailer may each connect to a lower connecting pipe. The lower connecting pipes may extend downward, to one or more gravity flow pipes. The gravity flow pipes may be slightly sloped from the back of the trailer toward the front, so that wastewater will flow through the pipe toward the front of the trailer under the force of gravity. For a trailer with a 38' lower deck, the gravity flow pipe should have at least 4" of total drop (the end of the pipe at the front end of the lower deck should be at least 4" below the end at the rear end of the lower deck) for wastewater to flow properly. In some embodiments the drop will be sufficient for the gravity flow pipe to operate correctly when the trailer is parked on a level surface. If no level ground is available, the gravity flow pipe may still operate correctly if the trailer can be parked in a downhill orientation so that the drop will be greater than 4". In other embodiments where the system is mounted on a trailer or shipping container that is shorter or longer, a smaller or a greater drop may be required. In at least one embodiment, the gravity flow pipe has a 4" inner diameter. In other embodiments, other inner diameters may be used, for example, between 3" and 6", between 3" and 5", or between 3.5" and 4.5". One will appreciate that because the gravity flow pipe slopes from the rear end of the lower deck toward the front, the lower connecting pipe at the rearmost toilet will be shorter than the other lower connecting pipes, and each of the other lower connecting pipes will be slightly longer than the lower connecting pipe behind it, to accommodate the sloping of the gravity flow pipe.

In some embodiments there may be more than one gravity flow pipe, for example in embodiments with multiple rows of toilets there might be one gravity flow pipe for each row. There may also be multiple central flush water lines supplying water to the toilets. A single central flush water line may supply water to multiple rows of toilets if the upper connecting pipes are configured correctly to lead from the central flush water line to each toilet. Or there may be separate central flush water lines for each row of toilets.

In some embodiments the toilets may be mounted directly on the surface of the trailer. In these embodiments holes might be cut in the trailer bed to allow lower connecting pipes to run between the toilets and the gravity flow pipe. In other embodiments, the toilets may be mounted on a raised platform above the surface of the trailer, and the gravity flow pipe and lower connecting pipes may be below the platform but above the surface of the trailer. The platform might be between 1 and 2 feet above the surface of the trailer to allow enough space below the platform to accommodate pipes and other equipment beneath the platform.

In some embodiments, wastewater travels down one or more gravity flow pipes to a pump box disposed near the front of the lower deck. The pump box may be located in various places, but should be beneath the waste receptacles if wastewater must flow to the pump box by gravity. For example, in one particular embodiment, the pump box is directly beneath the front-most toilets. In this embodiment, the lower connecting pipe from the front-most toilet leads directly to the pump box, while all other lower connecting pipes lead to the gravity flow pipe, which in turn leads to the pump box. In other embodiments, all lower connecting pipes may lead to the gravity flow pipe, or all lower connecting pipes may lead directly to the pump box. The pump box may be located on the lower deck of the trailer, beneath a platform if the waste receptacles are on a raised platform. Or if mounted beneath the trailer, the pump box may be flush with the front end of the lower deck, or it may extend slightly past the front end of the lower deck, but it should not extend so far past the front end of the lower deck that it would interfere with a semi-truck pulling the trailer.

A pump box in a waste treatment system in accordance with the present invention may comprise a pump and waste holding tank, a pump and waste holding tank enclose together in an enclosure, a pump and waste holding tank combined into a single piece of equipment, or a pump alone. For example, in one particular embodiment, the pump box comprises a waste holding tank and a macerator pump. Wastewater first flows into the waste holding tank. The waste holding tank may be any suitable size, for example, between 10 gal and 50 gal, between 20 gal and 50 gal, or between 20 gal and 30 gal. The macerator pump grinds up solids in the wastewater, including organic solid waste and also unauthorized solids that users might flush down the toilets, such as diapers, plastic packaging, or other garbage. After grinding the solids, the macerator pump pumps the wastewater through an IBR feed line to an inlet on an IBR. In at least one embodiment, the macerator pump pumps wastewater to the IBR at a rate of 10 gal/min and at a pressure sufficient to transport the wastewater to the IBR (pressures around 2 to 4 ft. of water should be sufficient). The macerator pump may be configured to run continuously, or it may be configured to run at set intervals based on a timer, or there might be a level sensor on the waste holding tank that would send a signal to start the macerator pump when the wastewater reaches a certain level. In other embodiments, the pump box may comprise a macerator pump only, without a waste holding tank. In these embodiments the macerator pump should run continuously or at intervals often enough to clear the gravity flow pipe so wastewater does not back up in the toilets.

A wastewater pump in waste treatment systems in accordance with the present invention may connect to an anaerobic digester through piping. For example, in one particular embodiment, a macerator pump may connect to an IBR through an IBR feed line. The IBR feed line may include any bends or elbow joints necessary to reach from the outlet of the macerator pump to the inlet of the IBR. If the pump box is mounted on the bottom of a trailer, then the IBR feed line may follow a path around the edge of the trailer bed, or it may go through an opening in the trailer bed. For pump boxes beneath a raised platform, there may be a space between the frontward edge of the raised platform and the rise between the lower deck and upper deck of the trailer so the IBR feed line can run from the pump box to the IBR through the space.

Waste treatment systems in accordance with the present invention include an anaerobic digester. Various types of anaerobic digesters may be used. In one or more preferred embodiments, the anaerobic digester is an induced sludge blanket reactor, induced bed reactor, or IBR. The anaerobic digester may be various sizes depending on the size of the system and the throughput capacity that may be required. For example, in one particular embodiment, an IBR 60" in diameter is mounted on the upper deck of a drop deck trailer. In this particular embodiment, the IBR may extend above the top of a semi-truck cab, but is not so tall that it would exceed interstate highway height limits, typically 14' above the roadway. The inlets, outlets, septum, and other components of the IBR are arranged according to the disclosure of U.S. Pat. No. 7,452,467. The IBR can process up to 10 gal wastewater per minute. Because the bacteria inside the IBR break down organic solids, the solids must remain in the reactor long enough to be broken down. Liquid can pass through the reactor more quickly, however. The holding time of liquid, or hydraulic retention time, is about $\frac{1}{20}^{th}$ of the solids retention time. Once started, the IBR can retain high efficiency even after long term storage. If storage exceeds several years, then it can easily be drained and restarted using sludge from a sewage treatment plant or even concentrated microorganisms available commercially from various sources. An anaerobic digester in other embodiments may need to be configured to smaller or larger sizes if the system is mounted on a smaller or larger trailer or container, and if less or more waste treatment capacity will be required.

Waste treatment systems in accordance with the present invention may include a means for breaking up organic solids in the wastewater stream, such as a macerator pump. It may also be necessary to break up other solids that users could flush down a toilet, such as paper or plastic waste. In one particular embodiment, solids are broken up by a macerator pump before entering an IBR. Unauthorized solids such as diapers and plastics will not harm the IBR, and they can be removed periodically by draining the IBR and physically removing these materials through a port in the bottom of the IBR. Removal of grit and sand in an operating IBR generally does not have to take place more than about once in five years, but can be removed by the same process as needed. Organic solids will eventually be broken down by the bacteria in the IBR. If excess liquid builds up in the system, it can be removed through a liquid outlet tap and used to water crops or for other purposes Likewise, if the liquid level in the system falls too low for the system to operate effectively, more water can be added through a liquid inlet on the IBR.

Anaerobic digesters in waste treatment systems in accordance with the present invention may contain bacteria that metabolize materials present in organic solid waste, thereby converted some of the organic solid waste into biogas. Various bacteria may perform various steps in the process of converting waste to biogas. Also, different bacteria may grow best in different conditions, such as different temperatures and pH ranges. Running the anaerobic digester at different temperatures may have different effects on the contents of the digester, such as killing pathogenic bacteria when run at high temperatures. For example, in one particular embodiment, the IBR is run in the thermophilic temperature range (50-60° C. or 120-140° F.). In this range, all pathogenic bacteria will be killed, while the bacteria used to break down organic solids will thrive. When necessary to maintain the temperature of the IBR, it may be heated with electrical heaters, with hot water from a water heater, or directly with a burner burning biogas from the gas conditioner. The IBR may optionally be insulated to retain heat. The IBR can also be run at mesophilic temperatures (such as 20-45° C.), but if it is run at mesophilic temperatures then water from the IBR should not be recycled to the toilets. It may still be used safely for watering crops. The water can be heat treated separately to kill pathogens if it is desired to recycle the water.

Waste treatment systems in accordance with the present invention include a means for transporting biogas from an anaerobic digester to a gas conditioner. For example, in one particular embodiment, biogas formed in an IBR is collected in a gas trap at the top of the IBR. The biogas exits through a biogas outlet and travels through a biogas line to a gas conditioner. In this particular embodiment, the gas conditioner comprises zeolite beds located in one or more structures that provides heat exchanges in accordance with the disclosure of U.S. Patent Application Pub. No. 2011/0041689. The zeolite removes impurities in the biogas such as $CO_2$, $H_2S$, and $H_2O$. The purified biogas will burn better and have fewer odors. In some embodiments the purified biogas is odor free.

Purified biogas produced in waste treatment systems in accordance with the present invention may be used for various purposes. The biogas may run one or more electric generators to supply electricity for the waste treatment system, as well as for other external systems. Because biogas is high in methane, it is similar to natural gas, and could power any type of generator that might be powered by natural gas. Such generators may include internal combustion engine generators, methane fuel cell generators, gas turbines, and others. The electric generator may power equipment within the waste treatment system, such as the flush water pump, the wastewater pump, the anaerobic digester, the gas conditioner, lighting in stalls, and any other electrical devices in the system. For example, in one particular embodiment, purified biogas flows out of the gas conditioner through a purified gas line to an electric generator which supplies electricity to a flush water pump, a macerator pump, an IBR, a gas conditioner, and lighting in toilet stalls. The electric generator may provide electricity to electric heaters that heat an IBR to its operating temperature. In other embodiments, an electric generator may supply electricity to the waste treatment system and external systems at the same time. External systems may include a distiller for purifying drinking water, or buildings such as a field hospital or machine shop. The amount of electricity generated may vary depending on the amount of waste the system processes. For example, a system that processes waste from 1500 users per day may produce up to 10 kW of continuous electric power for use outside the system. In further embodiments, biogas may be burned to provide heating, cooking, or lighting, or may fuel an internal combustion engine. In some embodiments a biogas-fueled internal combustion engine might drive the pumps in the waste management system, or the biogas might be used to heat an IBR, for example by fueling a burner that heats the IBR directly. In some embodiments, biogas may provide a combination of electrical power, mechanical power, and heating by fueling an internal combustion electric generator mechanically connected to pumps in the waste treatment system with exhaust directed through a heat exchanger to heat an IBR. Biogas may also be burned off-site in cooking stoves, gas lamps, or gas heaters. Biogas may be stored and transported to other locations for use elsewhere.

In some embodiments, a passive electric generator or a battery may provide additional electrical energy. A battery would be useful to provide electrical energy during startup of a waste treatment system, before the cycle begins producing enough energy to be self-sustaining. An alternative to a battery might be a stored supply of biogas or natural gas to run an electric generator for a period of time. A passive electric generator such as solar cells might provide charge to a battery and provide increased generation of electricity by the system.

Waste treatment systems in accordance with the present invention include a means for recycling water from an anaerobic digester to be used for flushing waste receptacles. The anaerobic digester may be connected directly to the waste receptacles through piping, or there may be pumps, tanks, water purifiers, or other devices between the digester and the waste receptacles. For example, in one particular embodiment, treated water from an IBR exits through an IBR effluent outlet. The water may flow by gravity through an effluent line to a water collection tank. Optionally the water may pass through a heat exchanger to pre-heat the waste stream in an IBR feed line. The water collecting tank may be of the same diameter as the IBR. The tank may be as tall as the IBR or shorter than the IBR. The outlet of the water collecting tank may lead to the 500 W pump, or some other pump, that is used to pressurize the water in a central flush water line. The water collecting tank may also have an outlet tap and an inlet for removing or adding water. Excess water may be removed to use in watering crops or other applications. Water may be added to the water collecting tank if the liquid level in the system drops too low. Preferably, the system will require little or no external water while operating. For example, 90% to 100% of the water necessary for flushing waste receptacles may be provided by recycling water from the anaerobic digester. At startup of the system, water may be added to the water collection tank to provide flush water to toilets and begin the cycle of recycling wastewater back to the water collection tank. Water can be added through a water filling inlet near the top of the water collecting tank.

A waste treatment system in accordance with the present invention may be easily transported. Systems mounted on semi-truck trailers may be transported by trucks or airlifted to a new location. Similarly, systems mounted in shipping containers may be transported by ship, train, or air. In some embodiments, a substantial amount of liquid can be drained before transport to decrease the weight of the system. For example, in one particular embodiment which includes a water collecting tank and an IBR, the water collecting tank can be drained before transportation to reduce the weight of the system. Also, three quarters (¾) of the liquid in the IBR may be drained before transport. The other ¼ of the liquid and the organic solids inside the IBR should remain, so that the IBR can be started again at the destination. If the IBR is stored without running for a long period of time, such as more than a year, so that the bacteria in the IBR have died, then the IBR may need to be completely drained and restarted with sludge from a local sewer or with commercially available bacteria. Sludge, bacteria, or water can be added to the IBR through an IBR filling inlet near the top of the IBR.

2. Representative Embodiments

Figure 1:
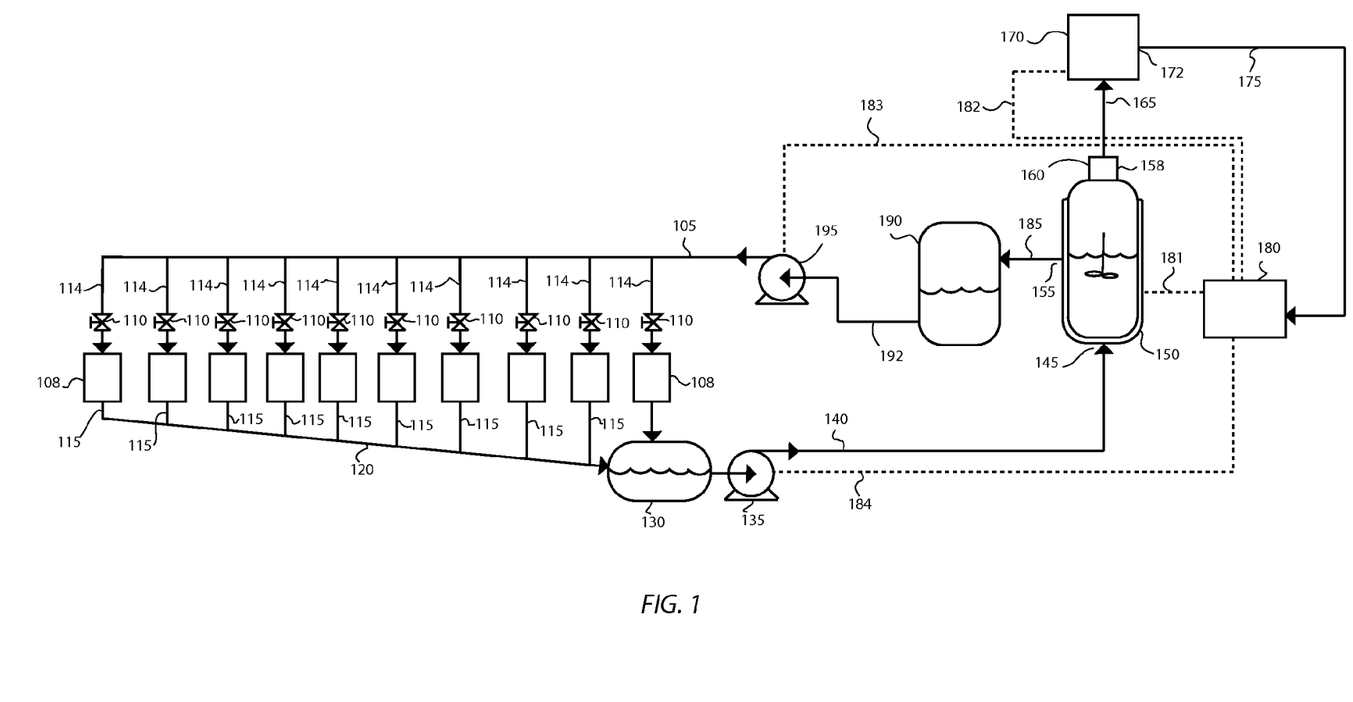
FIG. 1 is a schematic diagram of a portable human waste treatment system, in accordance with an embodiment of the present invention.

FIG. 1 is a schematic diagram of a portable human waste treatment system in accordance with an embodiment of the present invention. In this embodiment, a flush water pump 195 supplies pressurized water to a central flush water line 105. Water flows from the central flush water line 105 into ten upper connecting pipes 114. The upper connecting pipes 114 lead to ten flush valves 110. Each flush valve 110 is connected to a toilet 108. The flush valves 110 are maintained in a closed position, except that when a toilet 108 is flushed, the corresponding flush valve 110 opens for a short time to supply water for flushing.

When a toilet 108 is flushed, the human waste and water from the flush flow through a lower connecting pipe 115. Nine of the lower connecting pipes 115 lead to a gravity flow pipe 120. The gravity flow pipe 120 is sloped downward so that the wastewater in the gravity flow pipe 120 will flow to the lower end of the gravity flow pipe 120. The lower end of the gravity flow pipe 120 is connected to a waste holding tank 130. Wastewater in the gravity flow pipe 120 flows freely into the waste holding tank 130. The tenth lower connecting pipe 115, which does not lead to the gravity flow pipe 120, leads directly to the waste holding tank 130. Wastewater from the tenth toilet flows through this lower connecting pipe 115 and directly into the waste holding tank 130.

Wastewater flows out of the waste holding tank 130 to a macerator pump 135. The macerator pump 135 breaks up solids in the wastewater, and then pumps the wastewater into the IBR feed line 140. The wastewater flows from the IBR feed line 140, through the IBR inlet 145, and into the IBR 150. Inside the IBR 150, organic solids in the wastewater are digested by bacteria, forming biogas. The biogas is collected in a gas collector 158 at the top of the IBR 150. Biogas flows out through a biogas outlet 160 into a biogas line 165. From the biogas line 165, the biogas flows into a gas conditioner 170, where impurities in the biogas are removed. Purified biogas flows out of the gas conditioner 170 through a purified gas outlet 172 and into a purified gas line 175. From the purified gas line 175, the gas flows into an electric generator 180, where the gas is burned to produce electricity. The generator provides electricity to the IBR 150 through the IBR power wire 181, to the gas conditioner 170 through the gas conditioner power wire 182, to the flush water pump 195 through the flush water pump power wire 183, and to the macerator pump 135 through the macerator pump power wire 184.

Water exits the IBR 150 through an IBR effluent outlet 155. The water flows through an effluent line 185 into a water collecting tank 190. The flush water pump 195 draws water from the water collecting tank 190 through a water outlet line 192, and the water is recycled to the central flush water line 105 to be used for flushing toilets 108.

Figure 2:
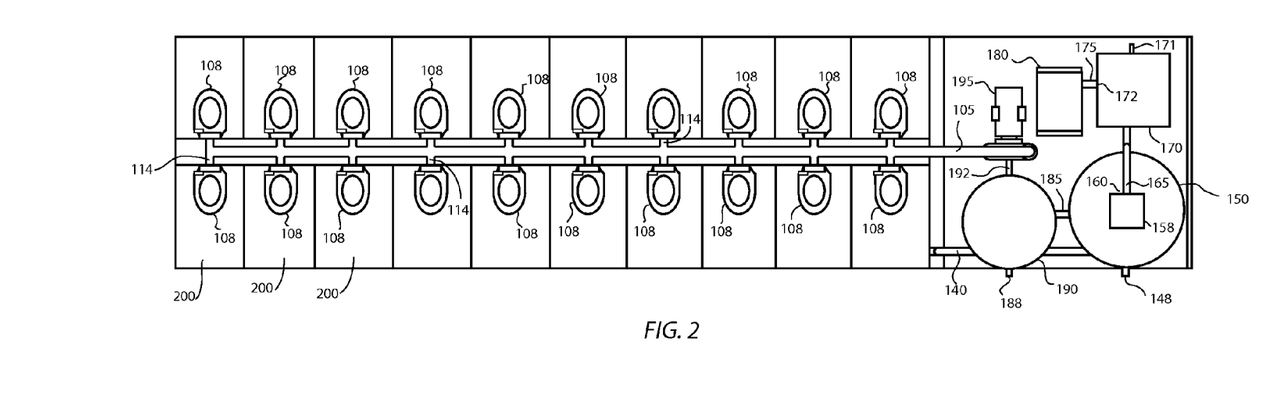
FIG. 2 is a top down view of a portable human waste treatment system in accordance with an embodiment of the present invention.
Figure 3:
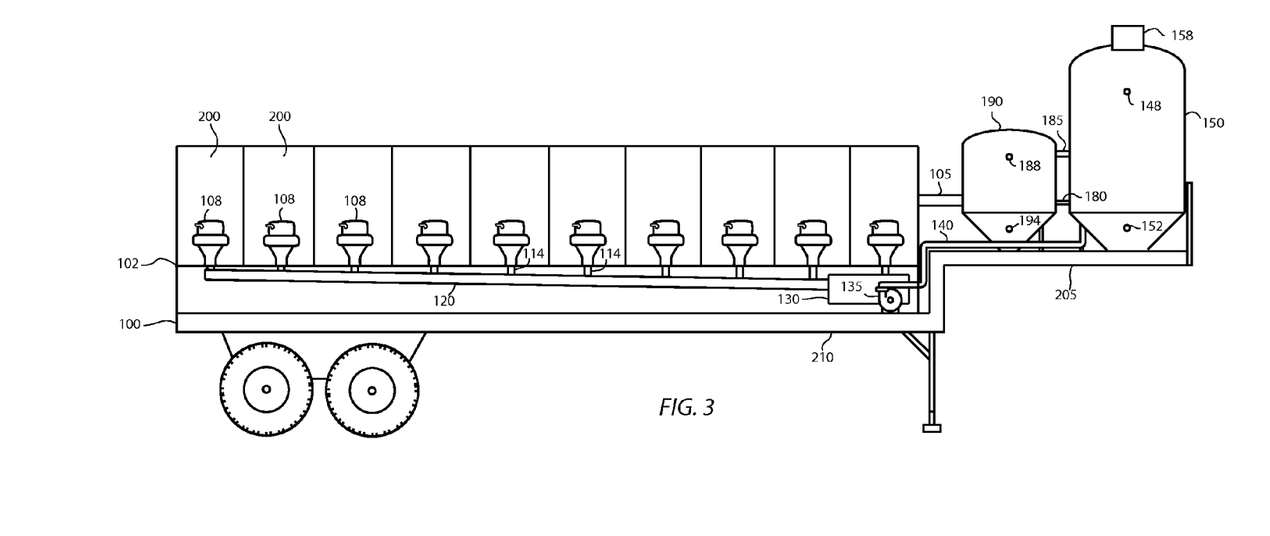
FIG. 3 is a side view of a portable human waste treatment system in accordance with an embodiment of the present invention.
Figure 4:
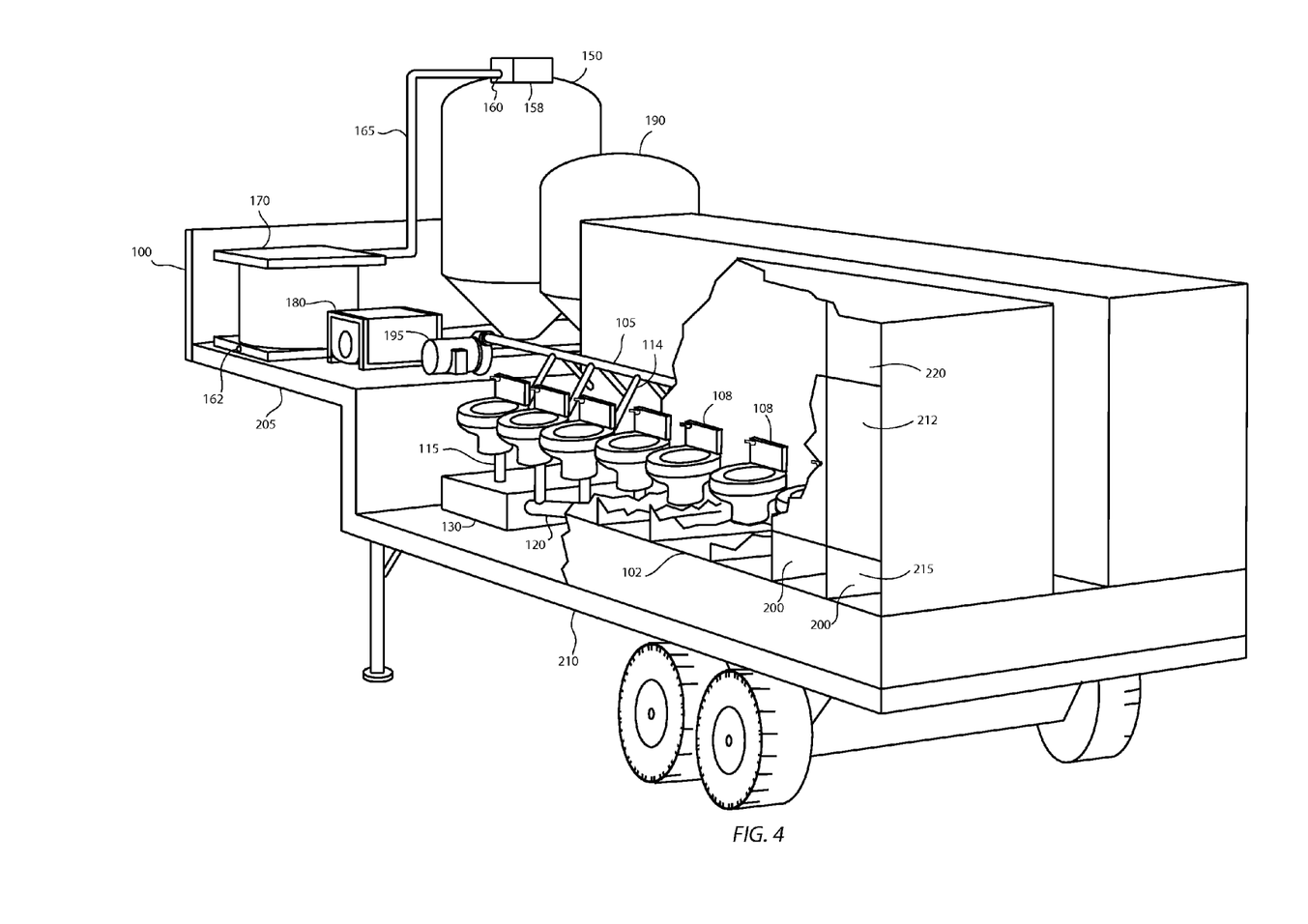
FIG. 4 is a perspective view of a portable human waste treatment system in accordance with an embodiment of the present invention.

FIG. 2, FIG. 3, and FIG. 4 are a top-down view, a side view, and a perspective view, respectively, of a portable human waste treatment system in accordance with an embodiment of the present invention. In this embodiment, a portable human waste treatment system is mounted on a drop-deck semi-truck trailer 100. A flush water pump 195 is mounted near the rear of the upper deck 205 of the trailer 100. The flush water pump 195 supplies pressurized water to a central flush water line 105, which runs along the center of the trailer 100 toward the rear of the trailer 100. Water flows from the central flush water line 105 into twenty upper connecting pipes 114. Each upper connecting pipes 114 leads to a toilet 108.

The toilets 108 are arranged in two rows of ten each. The rows face outward from the center of the trailer, one row facing right and the other facing left. Each toilet 108 is enclosed in a stall 200, with a door 212 on the front of each stall 200. The height of the doors 212 is less than the height of the stalls 200, so that there is an under-door space 215 under each door and an above-door space 220 above each door 212. The toilets 108 and stalls 200 are mounted on a raised platform 102, between 1 and 2 feet above the lower deck 210 of the trailer 100.

The toilets 108 each include a flush valve which is maintained in a closed position when not flushing, and which opens when a flush lever on the toilet 108 is manually pressed. When a toilet 108 flushes, water flows from the corresponding upper connecting pipe 114 into the bowl of the toilet 108 to carry waste down the drain and out of the toilet 108.

Human waste and water from flushes from the twenty toilets 108 flow through twenty lower connecting pipes 115. Eighteen of the lower connecting pipes 115 lead to two gravity flow pipes 120. The first nine lower connecting pipes 115 from the left row of toilets 108 lead to a left gravity flow pipe 120, and the first nine lower connecting pipes 115 from the right row of toilets 108 lead to a right gravity flow pipe 120. The gravity flow pipes 120 are mounted beneath the raised platform 102, directly below each row of toilets 108. The gravity flow pipes 120 are sloped downward so that the wastewater in the gravity flow pipes 120 will flow to the lower end of the gravity flow pipes 120. The lower ends of the gravity flow pipes 120 are connected to a waste holding tank 130. The waste holding tank 130 is mounted on the lower deck 210 of the trailer 100, near the front end of the lower deck 210 and directly below the two front-most toilets 108. Wastewater in the gravity flow pipes 120 flows freely into the waste holding tank 130. The last lower connecting pipe 115 on each row, which do not lead to either of the gravity flow pipes 120, lead directly to the waste holding tank 130. Wastewater from the toilets 108 connected to these lower connecting pipes 115 flows through these lower connecting pipes 115 and directly into the waste holding tank 130.

Wastewater flows out of the waste holding tank 130 to a macerator pump 135. The macerator pump is mounted on the lower deck 210 of the trailer 100 to the right of the waste holding tank 130. The macerator pump 135 breaks up solids in the wastewater, and then pumps the wastewater into the IBR feed line 140. The wastewater flows from the IBR feed line 140 into the IBR 150. The IBR 150 is mounted on the upper deck 205, near the front of the trailer 100. Inside the IBR 150, organic solids in the wastewater are digested by bacteria, forming biogas. The biogas is collected in a gas collector 158 at the top of the IBR 150. Biogas flows out through a biogas outlet 160 into a biogas line 165. From the biogas line 165, the biogas flows into a gas conditioner 170, where impurities in the biogas are removed. The gas conditioner 170 is made up of a number of zeolite beds, packed in heat exchangers (not shown). The gas conditioner 170 is mounted on the upper deck 205 to the left of the IBR 150. Purified biogas flows out of the gas conditioner 170 through a purified gas outlet 172 and into a purified gas line 175. From the purified gas line 175, the biogas flows into an electric generator 180, where the biogas is burned to produce electricity. The generator 180 is mounted on the upper deck 205 just behind the gas conditioner 170. Purified biogas can also be removed from the gas conditioner 170 through an auxiliary purified gas outlet 171.

Water exits the IBR 150 through an IBR effluent outlet. The water flows through an effluent line 185 into a water collecting tank 190. The water collecting tank is mounted on the upper deck 205, just behind the IBR 150. The flush water pump 195 draws water from the water collecting tank 190 through a water outlet line 192, and the water is recycled to the central flush water line 105 to be used for flushing toilets 108.

Water can also be removed from the water collecting tank 190 through an auxiliary water outlet 194 located near the bottom of the water collecting tank 190. Additional water can be added to the water collecting tank through a water filling inlet 188 located near the top of the water collecting tank 190. The IBR 150 can be drained of wastewater through an IBR draining outlet 152 located near the bottom of the IBR 150. Also, water or sludge can be added to the IBR 150 through an IBR filling inlet 148 located near the top of the IBR 150.

It should be appreciated that the methods and apparatus of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed is:

1. An apparatus for treatment of human waste and production of energy, comprising: a. one or more human waste receptacles; b. at least one anaerobic digester configured to receive human waste from said one or more human waste receptacles, digest organic matter in said human waste, and produce treated water treated solids and treated biogas; and, c. at least one gas conditioner configured to receive said biogas and remove impurities from said biogas, wherein the one or more human waste receptacles, the at least one anaerobic digester, and the at least one gas conditioner are disposed within a container, wherein the volume of the container is less than 6,600 cubic feet, and wherein said gas conditioner comprises: a. an upper manifold; b. a lower manifold; c. an inlet configured to receive a biogas stream comprising impurities; d. at least one heat exchange member disposed between the upper manifold and the lower manifolds, the heat exchange member comprising a thermally conductive material so as to draw heat away from and/or transfer heat into a zeolite bed or other contents in heat transferring contact with the heat exchange member; e. a bed comprising zeolite in heat exchanging contact with the heat exchange member, wherein the heat exchange member comprises a thermally conductive material so as to draw heat away from the zeolite bed as the biogas stream containing impurities is introduced through the inlet so as to contact the zeolite bed such that the zeolite adsorbs at least some of the impurities within the biogas stream containing impurities; and f. an outlet configured to receive a conditioned biogas stream from which impurities have been removed and to be a conduit for the conditioned biogas as the conditioned biogas is being removed from the gas conditioner.

2. An apparatus for treatment of human waste and production of energy, comprising: a. one or more human waste receptacles; b. at least one anaerobic digester configured to receive human waste from said one or more human waste receptacles, digest organic matter in said human waste, and produce treated water treated solids and treated biogas; and, c. at least one gas conditioner configured to receive said biogas and remove impurities from said biogas, wherein the one or more human waste receptacles, the at least one anaerobic digester, and the at least one gas conditioner are disposed within a container, wherein the volume of the container is less than 6,600 cubic feet, and wherein the apparatus further comprises a water purification device wherein the water purification device is a) configured to receive flushed water from the one or more human waste receptacles and to treat the flushed water and remove minerals from the flushed water to form treated water for flushing human waste receptacles, b) coupled to the one or more human waste receptacles so that treated water can flow from the water purification device to the one or more human waste receptacles, and c) configured to treat flushed water to form drinkable water, wherein the apparatus further comprises a generator, wherein the generator is configured to receive conditioned biogas and to use the conditioned biogas to provide sufficient power for the water purification device wherein the water purification device is configured to remove pathogenic organisms.

3. The apparatus of claim 2, wherein said one or more human waste receptacles comprises at least three human waste receptacles, said at least one anaerobic digester, and said at least one gas conditioner are mounted in a container, wherein the combined weight of the apparatus and the container is less than 11,000 pounds and wherein the apparatus further comprises a computer receiving power from the generator configured to receive conditioned gas, and wherein the computer is configured to operate the water purification device, the anaerobic digester, and the generator.

4. The apparatus of claim 3, wherein said container is configured to be coupled to an aircraft and hoisted by an aircraft at least 20 feet in the air, wherein said one or more human waste receptacles comprise at least 20 toilets.

5. The apparatus of claim 2 wherein the generator is at least one selected from the group consisting of an energy generator and a fuel cell.

6. The apparatus of claim 3 wherein the container is at least one selected from the group consisting of a semi-truck trailer and a shipping container.

* * * * *